US00PP18560P3

(12) United States Plant Patent
Korlipara

(10) Patent No.: US PP18,560 P3
(45) Date of Patent: Mar. 4, 2008

(54) *COREOPSIS* PLANT NAMED 'SNOWBERRY'

(50) Latin Name: ***Coreopsis* hybrid**
Varietal Denomination: Snowberry

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 7 days.

(21) Appl. No.: 11/474,021

(22) Filed: Jun. 23, 2006

(65) Prior Publication Data

US 2007/0300339 P1 Dec. 27, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct *Coreopsis* plant named 'Snowberry' characterized by large, daisy-type flowers that are about 4.5 cm in diameter; unique primrose yellow and maroon bi-colored ray florets; grass green foliage; very free branching; very free flowering; and mounding habit.

1 Drawing Sheet

Botanical denomination: *Coreopsis* ssp. (*Coreopsis* 'Limerock Ruby'×*Coreopsis auriculata* 'Nana').

Variety designation: 'Snowberry'.

Cross reference to sibling: *Coreopsis* 'Autumn Blush' (U.S. Plant patent application Ser. No. 11/452,687).

BACKGROUND OF THE INVENTION

The present invention relates to a new and distinct hybrid of *Coreopsis* and given the cultivar name 'Snowberry'. *Coreopsis* is in the family *Asteraceae*. This new cultivar originated from a controlled cross of *Coreopsis* 'Limerock Ruby' (U.S. Plant patent application publication No. 20030066114), as the seed parent and *Coreopsis auriculata* 'Nana', an unpatented plant, as the pollen parent.

SUMMARY OF THE INVENTION

The following traits have been repeatedly observed and are determined to be the unique characteristics of the new variety. These characteristics in combination distinguish *Coreopsis* 'Snowberry' as a new and distinct cultivar.

1. Large daisy-type flowers that are about 4.5 cm in diameter.
2. Unique primrose yellow and maroon bi-colored ray florets.
3. Grass green foliage.
4. Very free branching.
5. Very free flowering.
6. Mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Snowberry' growing in the ground in the trail field in August in Canby, Oreg.

DETAILED PLANT DESCRIPTION

The following is a detailed description of the new *Coreopsis* cultivar based on observations of a one-year-old specimen growing in the ground in full sun under typical outdoor conditions in the trial fields in August in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 5 to 9.
- *Size.*—50 cm wide and 40 cm tall to top of inflorescences.
- *Form.*—Mound.
- *Vigor.*—Excellent.
- *Roots.*—Fibrous, Grey Brown 199D, stems root easily from stem cuttings.

Stem:
- *Type.*—Ascending.
- *Size.*—52 cm tall and 4 mm wide.
- *Internode length.*—5 to 9.5 cm.
- *Surface.*—Sparsely pubescent.
- *Color.*—Yellow Green 137A.

Leaf:
- *Type.*—Compound, pinnate.
- *Shape.*—Ovate, cupped.
- *Lobing.*—5 to 6 pinnatifid, linear, each lobe 1 to 2.5 mm wide and 2 to 3.5 cm long, except lowest leaves which are three lobed with the terminal lobe the longest and widest, elliptic, 12 mm wide and 75 mm long.

*Arrangement.*—Opposite.

*Length including petiole.*—Grows to 17 cm.

*Width.*—5 to 7 cm.

*Margins.*—Entire.

*Apex.*—Acute.

*Surface texture.*—Glabrous, rubbery to the touch.

*Venation.*—Pinnate.

*Color.*—Top side — Closest to Yellow Green 146A Bottom — Closest to Yellow Green 146A.

*Petiole.*—Length variable, width 1 to 3 mm, margins pubescent, Yellow Green 146A.

Inflorescence:

*Type.*—Long stalked terminal heads of daisy type inflorescences.

*Peduncle.*—6 to 9 cm tall, 1 mm wide, glabrous, Yellow Green 146A.

*Size.*—4.5 cm wide and 11 mm deep.

*Immature.*—10 mm long and 7 mm wide, ovoid, glabrous, Greyed Yellow 161A on top and Yellow Green 146A on bottom.

*Receptacle.*—Bowl shaped, 10 mm wide and 5 mm deep, Green 137A.

*Phyllary.*—In two series; inner series broadly campanulate with 8 lobes, grows to 2 cm wide and 1 cm deep, each lobe ovate, entire, acute, glabrous, 13 mm long and 5 mm wide, on both sides top half Yellow Green 153A edged with Orange 24D, bottom half Yellow Green 146A; outer series stellate, with 8 lobes, grows to 15 mm wide and 5 mm deep, lobes lanceolate, entire, acute, 7 mm long and 2 mm wide, Green 137A on both sides.

*Lastingness.*—Each inflorescence last about a week on the plant.

Florets:

*Type.*—Composite.

*Ray florets.*—8 in number with no pistil or stamen, obovate with the tip three lobed with lobes obtuse and notched and the central lobe the longest, entire, grows to 21 mm long, 15 mm wide, glabrous. Ray floret, topside — Yellow 4D on top ⅔ and Red Purple 59A on the lower ⅓. Ray floret, bottom side — Yellow 4D on top ⅔ and Grey Brown 199B on the lower ⅓.

*Disc.*—Conic, deeper with maturity, 14 mm wide and becoming 6 mm deep with maturity, Orange Red 31A when in bud, opening to Yellow Orange 17A.

*Disc florets.*—About 130 in number, 6 mm long and 1 mm wide, tubular, Orange 28A at the apex to Yellow Orange 12B near base.

*Pistil* (*in disc florets only*).—1, ovary 2 mm long. Yellow Green 145C, style 5 mm long, extruding, with 2-branched stigma, stigma and style Orange 24A.

*Stamen* (*in disc florets only*).—5, filaments 2.5 mm long, Black 202A, pollen Yellow 13B.

*Bloom period.*—June through September in Canby, Oreg.

*Fragrance.*—Light, Chrysanthemum-like.

Seed: none produced.

*Fertility.*—Infertile.

Disease and pests: *Coreopsis* are susceptible to mildew and fungal spots. No resistance is known for this variety.

COMPARISONS TO SIMILAR *COREOPSIS*

Compared to *Coreopsis auriculata* 'Nana', an unpatented plant and the pollen parent, this new cultivar has similar inflorescence size and ray petal shape but with narrow leaves, bicolor ray florets of very light yellow and maroon, instead of yellow orange, and a larger habit.

Compared to the seed parent, *Coreopsis* 'Limerock Ruby' mutant, the new variety has bicolor ray florets of very light yellow and maroon rather than ruby red.

Compared to *Coreopsis rosea* 'Sweet Dreams' (U.S. Plant Pat. No. 12,720), this new cultivar has larger bicolor ray florets of very light yellow and maroon rather than purple and white. Both are freely branching and flowering with an outwardly spreading habit.

Compared to *Coreopsis* 'autumn Blush', a sibling cross, the new variety has lighter yellow ray floret color.

I claim:

1. A new and distinct *Coreopsis* plant as herein illustrated and described.

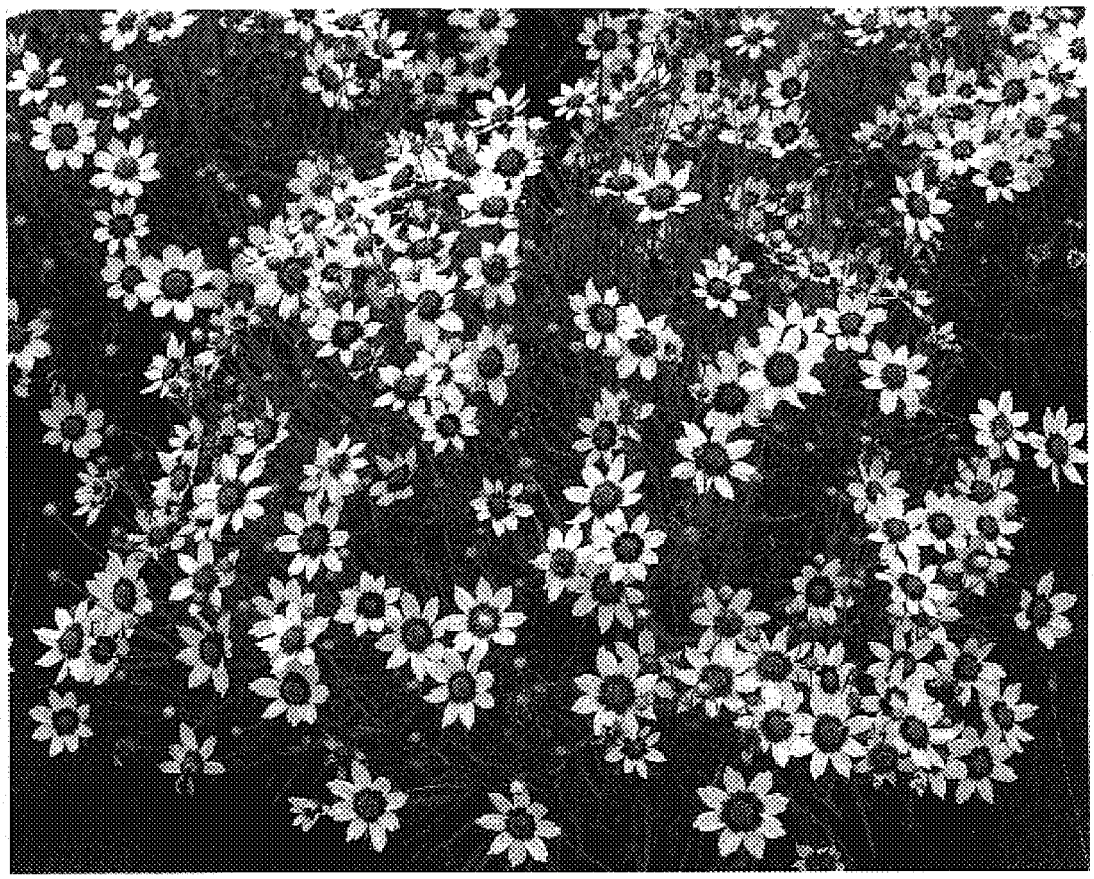

* * * * *